(12) United States Patent
DiBenedetto et al.

(10) Patent No.: US 7,727,542 B2
(45) Date of Patent: *Jun. 1, 2010

(54) BIOACTIVE MATERIALS, METHODS OF MAKING BIOACTIVE MATERIALS AND METHOD OF USE THEREOF

(75) Inventors: Anthony T. DiBenedetto, Mansfield Center, CT (US); Samuel Jien-shek Huang, Mystic, CT (US); Claudio Migliaresi, Tenna (IT); Antonella Motta, Milano (IT)

(73) Assignee: University of Connecticut, Storre, CT (US)

( * ) Notice: Subject to any disclaimer, the term of this patent is extended or adjusted under 35 U.S.C. 154(b) by 785 days.

This patent is subject to a terminal disclaimer.

(21) Appl. No.: 10/281,096

(22) Filed: Oct. 25, 2002

(65) Prior Publication Data

US 2003/0099630 A1    May 29, 2003

Related U.S. Application Data

(60) Provisional application No. 60/343,006, filed on Oct. 25, 2001.

(51) Int. Cl.
*A61F 2/02* (2006.01)
*A61K 38/17* (2006.01)
(52) U.S. Cl. ..................... 424/426; 530/353
(58) Field of Classification Search ............. 424/426; 530/353, 817, 858
See application file for complete search history.

(56) References Cited

U.S. PATENT DOCUMENTS 4,233,211 A    11/1980    Ohtomo et al. .......... 260/123.7

(Continued)

FOREIGN PATENT DOCUMENTS

EP    0 513 803 A2    11/1992

(Continued)

OTHER PUBLICATIONS

Tsukada, M. et al.; "structural Changes of Silk Fibroin Membranes Induced by Immersion in Methanol Aqueous Solutions"; Journal of Polymer Science: Part B: Polymer Physics, vol. 32, (1994); pp. 961-968.*

(Continued)

*Primary Examiner*—Carlos A. Azpuru
(74) *Attorney, Agent, or Firm*—Cantor Colburn LLP (57) ABSTRACT

A bioactive material is made using fibroin solutions and suspensions that can be used alone or as a composite with particles such as core/shell particles. The material is designed to support the constructions, repair, regeneration or augmentation of bone and other tissues of the body. The solutions and suspensions can be loaded with core/shell-type particles comprising inorganic core materials that are coated with biodegradable polymers with an outer coating of a calcium phosphate precursor. The fibroin solutions, suspensions, and composites can be injected to fill cavities or to replace missing tissue. After injection, the materials can produce a scaffold capable of promoting tissue regeneration while degrading. The degradation of the particles, when present, can generate additional porosity within the scaffold and release other compounds in a controlled manner to enhance growth and activation of the cells necessary for tissue repair. The ability to inject the fibroin solutions, suspensions and composites can reduce the need for many types of surgical procedures that are used to replace or repair bone and other tissues.

30 Claims, 9 Drawing Sheets

U.S. PATENT DOCUMENTS

| | | | |
|---|---|---|---|
| 4,490,984 A | 1/1985 | Hongo et al. | 62/49 |
| 4,675,189 A | 6/1987 | Kent et al. | 424/490 |
| 4,818,291 A | 4/1989 | Iwatsuki et al. | 106/124 |
| 5,480,644 A | 1/1996 | Freed | 424/436 |
| 5,490,984 A | 2/1996 | Freed | 424/436 |
| 5,599,852 A | 2/1997 | Scopelianos et al. | 525/105 |
| 5,728,752 A | 3/1998 | Scopelianos et al. | 523/113 |
| 5,824,333 A | 10/1998 | Scopelianos et al. | 424/423 |
| 5,863,984 A | 1/1999 | Doillon et al. | 525/54.1 |
| 5,939,323 A | 8/1999 | Valentini et al. | 435/395 |
| 6,140,452 A | 10/2000 | Felt et al. | 528/60 |
| 6,218,357 B1 | 4/2001 | Terauchi | 514/2 |

FOREIGN PATENT DOCUMENTS

| | | |
|---|---|---|
| WO | WO 01/25403 A2 | 4/2001 |
| WO | WO 02/29141 A1 | 4/2002 |

OTHER PUBLICATIONS

Kesenci, K., et al; "Poly(e-casprolactone-co-D, L-lactide) / silk fibroin composite materials: preparation and characterization" *J. Biomater Sci Polym Ed 2001;* 12 (3): pp. 337-51.

Kurosaki, S., et al.; "Fibroin allergy"; *J. Nippon Med Sch 1999:* 66(1); pp. 41-44.

Motta, A., et al.; "Regenerated Silk Fibroin Films: Thermal and Cynamic Mechanical Analysis"; *Macromol. Chem. Phys. 2002,* 203, pp. 1658-1665.

Motta, A. et al.; "Silk Derived Fibroin Membranes for Biomedical Use"; *Third International Symposium on Frontiers in Biomedical Plymers Including Polymer Therapeutics—From Labroatory to Clinical Pracitce* Abstract, Shigha Japan, May 1999.

Santin, M., et al.; "In vitro evaluation of the inflammatory potential of the silk fibroin"; J. Biomed. Maker. Res 1999, 46(43): pp. 382-389.

Tsukada, M., et al.; "Structural Changes of Silk Fibroin Membranes Induced by Immersion in Methanol Aqueous Solutions"; *Journal of Polymer Science: Part B: Polymer Physics,* vol. 32, (1994); pp. 961-968.

Database WPI, Section Ch, Week 198123, Derwent Publications Ltd., London, GB; AN 1981-40786D XP002235614 & JP 56 040156 A (Kanebo Ltd), Apr. 16, 1981, Abstract.

Database WPI Section Ch, Week 200147, Derwent Publications Ltd., London,G B; AN 2001-433340 XP002235615 & CN 1 293 952 A (Univ Wuhan) May 9, 2001, Abstract.

Database WPI Section Ch, Week 199001 Derwent Publications Ltd., London, GB; AN 1990-004589 XP002235616 & JP 01 288269 A (TOA Nenryo Kogyo KK), Nov. 20, 1989, Abstract.

Yang G et al.: "Structure and microporous formation of cellulose/silk fibroin blend membranes—I Effect of coagulants" Journal of Membrane Science, Elsevier Science, Amsterdam, NL, vol. 177, No. 1-2, Aug. 30, 2000, pp. 153-161 XP004215319 ISSN: 0376-7388 ,Abstract.

Kweon H et al.: "Structural and thermal characteristics of *Antheraea pernyi* silk fibroin/chitosan blend film" Polymer, Elsevier Science Publishers B.V., GB, vol. 42, No. 15, Jul. 2001, pp. 6651-6656, XP004235369 ISSN: 0032-3861, Abstract.

Database WPI Section Ch, Week 198947, Derwent Publications Ltd., London, GB; AN 1989-343221, XP002235613 & JP 01 254621 A (Terumo Corp), Oct. 11, 1989, Abstract.

Havawa, et al.;"New Oral Dosage form for Elderly Patients: Preparation and Characterization of Silk Fibroin Gel"; Chem. Pharm. Bull,vol. 43, No. 2, 1995; pp. 284-288 .

Database PAJ; JP 11 18544 A (Minoura Norihiko); May 11, 1989.

International Search Report; International Application No. UCT PCT/US 02/34252; International Filing Date Oct. 25, 2002; Date of Mailing Apr. 8, 2003.

* cited by examiner

Acc. V  Spot Magn  Det  WD ⊢─────┤ 50 μm
15.0 kV 4.0  500x  GSE  9.8  4.6 Torr  WSG. Cit 70%U

FIG. 3

Acc. V  Spot Magn  Det  WD ⊢―――⊣ 20 μm
15.0 kV 4.0  1000x  GSE 9.9   2.9 Torr WSG.G 45%U

BIOACTIVE MATERIALS, METHODS OF MAKING BIOACTIVE MATERIALS AND METHOD OF USE THEREOF

CROSS REFERENCE TO RELATED APPLICATIONS

This application claims priority from Provisional Application Ser. No. 60/343,006, filed Oct. 25, 2001, which is incorporated herein by reference in its entirety.

BACKGROUND

This disclosure relates to the field of bone and tissue repair, and in particular to materials for bone and tissue repair, methods of making the materials, and methods for use of the materials.

Replacement and repair of bone and other tissues following injury often requires the use of surgical procedures. More than 300,000 hip prostheses are implanted each year in the United States and Europe. Additionally, 10% of the population suffers from periodontal disease, and 30% will require a tooth implant during his/her lifetime. Other surgical procedures include cartilage repair and plastic surgery of soft tissues. It is thus desirable to create scaffold materials for tissue repair or reconstruction, particularly injectable materials that can eliminate the need for many invasive procedures. Such materials should be biocompatible, i.e., not cytotoxic or causing adverse reaction in the body and preferably bioactive, i.e., providing the developmental signals needed for mobilization of the cell activity required for tissue building. They are furthermore preferably resorbable, and capable of withstanding the stresses imposed by daily activity during repair.

Several different approaches to scaffolds for tissue repair have been suggested. Currently available materials for hard tissue repair such as demineralized bone, hydroxyapatite, tricalcium phosphates, and other inorganic materials are not as effective as biologically derived bioactive scaffolds. Hyaluronic acid has been used as a scaffold material as disclosed in U.S. Pat. No. 5,939,323. Another approach has been to use collagen-based materials as disclosed in U.S. Pat. Nos. 4,490,984 and 5,480,644. These materials, however, appear to be limited in their range of potential uses and applications because of poor mechanical properties, unpredictable degradation rates and, for collagen, the risk of immunogenic reactions and dangers related to potential contamination.

Membranes, films and fabrics containing fibroin, a protein component of silkworm silk, have been suggested as substrate materials for the growth of animal tissues and organs. In particular, PCT Application number WO 01/25403 describes the formation of fibroin membranes cast from water solution. The membranes were cast in containers into which growth medium and various cell types were added, and the fibroin membrane supported the growth of cells such as osteoblasts, epithelial cells, and hepatocytes. Fibroin membranes and films are also disclosed by Tsukada et al., in *Journal of Polymer Science: Part B: Polymer Physics* 32: 961-968, 1994; and by Motta et al., in "Third International Symposium on Frontiers in Biomedical Polymers Including Polymer Therapeutics From Laboratory to Clinical Practice", Abstract, Shigha Japan, May 1999. PCT Application WO 02/29141 describes the formation of fibroin non-woven fabrics made by treating fibroin cocoons with formic acid. The fibroin non-woven fabrics can be used to culture cells such as keratinocytes and fibroblasts. A drawback of using such fibroin membranes, films, or non-woven fabrics as a scaffolds for tissue repair in vivo is that invasive surgical procedures would be required in order to place the materials at the site to be restored.

Accordingly, there remains a need for bioactive scaffold materials for use both in vitro and in vivo, particularly materials that are biocompatible, bioactive, and resorbable. There further remains a need for bioactive scaffold materials that are readily applied to the site to be restored, preferably without use of invasive surgical procedures.

SUMMARY OF THE INVENTION

The above discussed and other drawbacks and deficiencies of the prior art are overcome or alleviated by composition comprising a fibroin solution or suspension. The fibroin solutions and suspensions are biocompatible, bioactive, and resorbable. In a particularly advantageous feature, the fibroin solutions or suspensions can be applied to a desired site by injection, which minimizes use of invasive surgical procedures.

Also disclosed is a method for the formation of a fibroin suspension, comprising heating a fibroin solution from about −20° C. to about 50° C. to form a fibroin suspension. Another method for the formation of a fibroin suspension comprises treating a fibroin solution with an agent effective to form a fibroin suspension. Effective agents comprise an acid, an alcohol, a proteolytic enzyme, a biocompatible polymer, or combinations comprising at least one or more of the foregoing agents.

Further disclosed is a method of tissue construction, comprising administering to a site to be constructed a fibroin solution or suspension in an amount effective to stimulate cell proliferation, and preferably tissue growth. Administration is preferably by injection. The above discussed and other features and advantages will be appreciated and understood by those skilled in the art from the following detailed description and drawings.

BRIEF DESCRIPTION OF THE DRAWINGS

Referring now to the exemplary drawings wherein like elements are numbered alike in the several FIGURES.

DETAILED DESCRIPTION OF THE PREFERRED EMBODIMENTS

Fibroin is a known polypeptide containing a combination of 18 different amino acids, with glycine, alanine, serine, and tyrosine making up approximately 90% of the polypeptide chain. It is generally accepted that fibroin consists of two major chains linked by a disulfide bond and having molecular weights of approximately 350,000 daltons (H-chain) and 25,000 daltons (L-chain). The available studies of fibroin show that the structure and morphology of manufactured products derived from fibroin are highly dependent on the processing conditions used to form them. It has been advantageously discovered herein that novel fibroin suspensions can be produced from fibroin solutions using a variety of techniques, and that the fibroin suspensions so produced have utility in tissue construction, including the formation of tissue at normal sites in the body (i.e., sites without injury) and sites in need of repair and/or reconstruction due, for example, to injury or aging. As used herein, a "fibroin solution" refers to composition having substantially one phase, that is, a composition comprising a solvent in which fibroin is substantially dissolved. Fibroin is substantially dissolved when greater than 95%, preferably greater than 98%, and most preferably greater than 99% of the fibroin, by weight, is in solution. Further as used herein, a "fibroin suspension" refers to a composition having two or more phases (i.e., a multi-phase material), with at least one phase comprising a solvent and at least one phase comprising fibroin. Without being held to theory, fibroin suspensions may exist in a variety of forms, for example, in the form of a colloid, an emulsion, as micelles, a sol or a gel.

For the purposes of describing the fibroin suspensions herein, reference will be made to "fibroin occlusions", "fibroin gels", fibroin creams", and "fibroin pastes", which may be characterized by readily observable physical characteristics such as appearance and relative viscosities. "Fibroin occlusion" refers to a fibroin suspension that is flowable on a level surface. Occlusions are often cloudy, i.e., exhibit some opacity. By flowable on a level surface, it is meant that a one cubic centimeter sample of the suspension will essentially immediately deform when deposited on a level horizontal surface. Without being held to theory, fibroin occlusions may be in the form of colloids, particularly sols, comprising dispersions of solid particles having dimensions of $10^{-9}$ to $10^{-6}$ meters in a continuous phase of the solvent.

A "fibroin gel" as used herein refers to a fibroin suspension that has gel-like physical characteristics, for example, plasticity, elasticity, or some degree of rigidity. Gels can be opaque or translucent, depending on the method used to form the gel. In contrast to an occlusion, a gel does not readily flow when placed on a level surface. A gel, however, can flow or deform when heat or mechanical stress, such as pressure, are applied, i.e., when the gel is reversible. Without being held to theory, a fibroin gel may contain a three-dimensional network of fibroin dispersed in the solvent.

A "fibroin cream" as used herein refers to a fibroin suspension that is more viscous than a fibroin occlusion. It is often white, and it is substantially non-flowable on a level surface. By substantially non-flowable on a level surface, it is meant that a one cubic centimeter sample of the fibroin cream will not appreciably deform within one minute of being deposited on a level, horizontal surface. Like fibroin gels, fibroin creams can deform when heat or mechanical stress are applied to the material.

A "fibroin paste" as used herein refers to a fibroin suspension that is highly viscous, and non-flowable when placed on a horizontal surface. By non-flowable on a level surface, it is meant that a one cubic centimeter sample of the fibroin paste will not appreciably deform within one hour of being deposited on a level, horizontal surface. The paste is deformable, however, under mechanical pressure.

Alternatively, the various types of fibroin suspensions may be described based on the injectability of the suspension through an aperture (i.e., of a needle) of a particular size. A fibroin occlusion or gel is readily injectable by hand through a small aperture needle such as a 20-gauge syringe needle having a diameter of about 584 micrometers. The fibroin cream is more viscous, and is therefore readily injectable by hand through a larger bore syringe needle, i.e., an 18 gauge needle having a diameter of about 838 micrometers. Pastes are not readily injectable by hand except through very large bore syringe needles, i.e., those having a diameter of greater than about 2 millimeters. It is to be understood that the classification of a fibroin suspension as an occlusion, gel, cream, or paste is for convenience only in describing use of fibroin suspensions.

The fibroin suspensions can be formed in vitro or in vivo. In vitro formation of fibroin suspensions can comprise treating a fibroin solution with an agent effective to form the suspension, such as heat, proteolytic enzymes, acids, alcohols, or a biocompatible polymer. Alternatively, fibroin suspensions can be formed in vivo by injecting or otherwise administering to an animal a fibroin solution. Without being held to theory, it is believed that after administration to a site in the body of an animal, a fibroin solution can rapidly dissipate excess water, thereby producing a suspension in the form of, for example, a gel. Fibroin suspensions can also undergo form changes in vivo. For example, a fibroin occlusion, after in vivo administration to a site in the body of an animal, can undergo a transition to form a fibroin gel.

A convenient source of fibroin is cocoons from the *Bombyx mori* silkworm which contain both fibroin and sericin proteins. Silks are fibrous proteins produced from spiders and different insects, the best known of which are silkworms (in particular the *Bombyx-mori* silkworm). Silk fibers have been used as sutures, but it has been found that braided silk sutures often produce a non-immunologic foreign-body reaction, causing granulomas even years after surgery (Kurosaki et al., Nippon Ika Daigaku Zasshi 66: 41-44, 1999). It has been confirmed, however, that the observed non-immunologic foreign-body reaction is caused by the presence of sericin in the native silk, and that pure fibroin does not provoke an immunological response.

Preferably, the fibroin is purified to remove toxins or other substances such as sericin that can cause adverse reactions in the body. Much of the sericin can be removed, for example, by degumming, i.e. washing in sodium carbonate with or without sodium dodecyl sulfate at 98° C.

The purified fibroin can then be dissolved in a solvent such as an aqueous solution of lithium bromide containing approximately 10% by weight of fibroin per unit volume. The fibroin solution may optionally contain other components such as buffers and other additives that do not significantly adversely affect the structure or stability of fibroin. The fibroin can be further purified preferably to greater than about 90%, more preferably greater than about 95%, and most preferably greater than about 99% by weight. The Lithium Bromide is removed by dialysis against distilled water and other impurities may be removed by filtration. Once purified, the fibroin can be freeze-dried to a powder and stored. Fibroin suspensions can then be formed from a pure fibroin solution by treating the solution with heat, proteolytic enzymes, acids, alcohols, or a biocompatible polymer.

In one embodiment, fibroin suspensions can be produced by thermal treatment of a fibroin solution. For instance, to produce a gel, the fibroin solution may be kept at about −20° C. for about 2 to about 24 hours, then heated to a temperature of about 4° C. to about 50° C. Modification of the thermal treatment conditions results in suspensions of varying attributes as described above, which can be selected by one of ordinary skill in the art based on the particular application.

In another embodiment, a fibroin suspension can be produced by treating the fibroin solution with proteolytic enzymes that are specific for cleavage between particular amino acids. Such proteolytic enzymes include but are not limited to the protease from *Streptomyces griseus*, papain, chymotrypsin, and the like. Without being bound by theory, it is hypothesized that proteolytic enzyme treatment can produce a suspension by reducing the average molecular weight of the fibroin polymer. Specific amino acid sequences can be selected to produce fragments having desired molecular weights and amino acid sequences. The fragment sizes can be tailored to meet specific demands of particular applications, such as bioactivity and degradation rate of the fibroin material. Selection of a particular average molecular weight will depend on a number of factors, including end use, desired viscosity, addition of other components, molecular weight distribution, type of carrier, and the like. The average molecular weights of the fibroin after proteolytic treatment are about 200 to about 0.1 kiloDalton (kD), preferably about 50 to about 0.2 kD, more preferably about 20 to about 0.5 kD.

In another embodiment, the fibroin suspension can be formed by treating a fibroin solution with an acid. Without being bound by theory, it is believed that by reducing the pH of the fibroin solution below its isoelectric point, the miscibility of the fibroin in the solvent will be reduced, thus promoting suspension formation. The acid is an acid capable of reducing the pH point of fibroin below its isoelectric point of pH 3.8 (i.e., less than or equal to about pH 3.7). Preferred acids are citric acid, ascorbic acid, lactic acid, combinations of the foregoing acids, and the like. The amount of acid added is that which is sufficient to reduce the pH of the solution to the desired pH, and can be readily determined by one of skill in the art.

The fibroin suspension can alternatively be formed by treating a fibroin solution with an alcohol. Without being bound by theory, it is believed that the alcohol can alter the fibroin protein conformation, thus promoting formation of a suspension. The alcohol is preferably miscible with the solvent, and can be, for example, glycerol, ethylene glycol, ethanol, isopropanol, and mixtures comprising one or more of the foregoing alcohols, and the like. A preferred alcohol is glycerol. When added to the fibroin solution, the alcohol is added in an amount of about 10 volume % to about 50 volume % of the total volume.

In yet another embodiment, a more viscous fibroin solution can be formed by mixing a fibroin solution with one or more biocompatible polymers such as, for example, polyethyleneglycol, polyethyleneoxide, polyvinylpyrrolidone, and the like. The biocompatible polymers should be miscible with the fibroin solution in an amount of about 2 to about 20% by weight.

Various additives can be used to improve the efficacy of the fibroin solutions and suspensions, for example, physiologically active agents that have a physiological activity such as a diagnostic or therapeutic activity. Accordingly, an active agent can include a detectable label (e.g., a radioactive label) that is useful for identifying the locations of the released agent in vivo. Active agents also include therapeutic agents that are useful for treating a disease or condition. Physiologically active agents include, for example, antibiotics or other compounds that inhibit infection; therapeutic agents for treating osteoporosis, other factors that act on bone and skeleton, bone morphogenetic proteins (BMPs), and other cytokines and the like that stimulate tissue growth, bone regeneration or wound healing. The physiologically active agent can also be a cell, for example a cell taken from a site of the patient and cultured on the fibroin suspension. In specific embodiments, the physiologically active agent comprises antibiotics, bone morphogenic proteins, compounds that stimulate tissue growth, compounds that stimulate bone regeneration, compounds that stimulate wound repair, cells, or a combination comprising one or more of the foregoing agents. In one embodiment, the physiologically active agent comprises compounds that stimulate bone regeneration.

Exemplary antibiotics include tetracycline, aminoglycosides, penicillins, cephalosporins, sulfonamide drugs, chloramphenicol sodium succinate, erythromycin, vancomycin, lincomycin, clindamycin, nystatin, amphotericin B, amantidine, idoxuridine, p-amino salicyclic acid, isoniazid, rifampin, antinomycin D, mithramycin, daunomycin, chlorexidine, adriamycin, bleomycin, vinblastine, vincristine, procarbazine, imidazole carboxamide, and the like.

Exemplary therapeutic agents for treating osteoporosis and other factors acting on bone and skeleton include calcium, alendronate, bone GLa peptide, parathyroid hormone and its active fragments, histone H4-related bone formation and proliferation peptide and mutations, derivatives and analogs thereof.

Exemplary cytokines include transforming growth factors (TGFs), fibroblast growth factors (FGFs), platelet derived growth factors (PDGFs), epidermal growth factors (EGFs), connective tissue activated peptides (CTAPs), osteogenic factors, and biologically active analogs, fragments, and derivatives of such growth factors. Members of the transforming growth factor (TGF) supergene family, which are multifunctional regulatory proteins, are particularly preferred. Members of the TGF supergene family include the beta transforming growth factors (for example TGF-beta 1, TGF-beta 2, TGF-beta 3); bone morphogenetic proteins (for example, BMP-1, BMP-2, BMP-3, BMP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), insulin-like growth factor (IGF)); Inhibins (for example, Inhibin A, Inhibin B); growth differentiating factors (for example, GDF-1); and Activins (for example, Activin A, Activin B, Activin AB). Growth factors can be isolated from native or natural sources, such as from mammalian cells, or can be prepared synthetically, such as by recombinant DNA techniques or by various chemical processes. In addition, analogs, fragments, or derivatives of these factors can be used, provided that they exhibit at least some of the biological activity of the native molecule. For example, analogs can be prepared by expression of genes altered by site-specific mutagenesis or other genetic engineering techniques.

The physiologically active agent can also be a differentiated or non-differentiated cell. Mesenchymal stem cells, for example, can be delivered to produce cells of the same type as the tissue into which they are delivered. Mesenchymal stem cells are not differentiated and therefore can differentiate to form various types of new cells due to the presence of an active agent or the effects (chemical, physical, etc.) of the local tissue environment. Examples of differentiated mesenchymal stem cells include osteoblasts, chondrocytes, and fibroblasts. Osteoblasts can be delivered to the site of a bone defect to produce new bone; chondrocytes can be delivered to the site of a cartilage defect to produce new cartilage; fibroblasts can be delivered to produce collagen wherever new connective tissue is needed; etc. The cells or genes may be either allogeneic or xenogeneic in origin. For example, the cells can be from a species other than the host species that have been genetically modified.

The physiologically active agents can simply be added to the fibroin solutions and suspensions or covalently bound to another component. Alternatively, the physiologically active agents can be added in controlled release form. One controlled release formulation contains the active agent dispersed or encapsulated in a slowly degrading, non-toxic, non-antigenic polymer such as copoly(lactic/glycolic) acid, as described by Kent et al. in U.S. Pat. No. 4,675,189. Additional slow release formulations will be apparent to the skilled artisan. See, for example, *Sustained and Controlled Release Drug Delivery Systems*, J. R. Robinson ed., Marcel Dekker, Inc., New York, 1978, and R. W. Baker, *Controlled Release of Biologically Active Agents*, John Wiley & Sons, New York, 1987.

In another embodiment, the fibroin solutions and suspensions can comprise organic, inorganic and/or protein inclusions of engineered size and chemical composition that affect factors such as porosity and biodegradation. In a preferred embodiment, the fibroin solution and/or suspension can further comprise particles such as core/shell particles that create additional porosity in the gel, thereby forming a scaffold after injection.

Exemplary organic or inorganic particles that can aid in bone growth and formation, include, for example, hydroxyapatite, tricalcium phosphate, marine animal derived particles such as corals and chitosans, and the like. In other embodiments, the core particles include a calcium phosphate-based mineral, a resorbable glass filler.

A preferred pore-forming particle is a core/shell particle in which an inorganic core is surrounded by a biodegradable organic shell. Such particles can serve as both a temporary support structure and an internal substrate for shaping a scaffold. The controlled biodegradation of the shells can provide additional porosity to the fibroin scaffold. Core/shell particles will be described in detail below.

The preferred core is an inorganic core. The composition, size, and shape of the inorganic core can be varied to meet the demands of different applications. For example, the core can be hydroxyapatite, tricalcium phosphate, or marine animal derived particles, such as corals and chitosans, to aid in bone ingrowth. The cores can have dimensions from about 1 nanometer to about 500 micrometers in their largest diameter, and be in the form of spheres, plates, fibers, and the like.

An optional reactive layer may be disposed on the core to enhance adhesion of the core to the polymer shell. Suitable reactive layers depend on the composition of the core and the shell, and are known in the art. A particularly useful class of compounds includes reactive titanates, zirconates, and silanes, for example, gammaglycidoxypropyltriethoxysilane.

The shell can comprise at least one biodegradable polymer. The composition and molecular weight of the polymer or polymers can be chosen to obtain an appropriate rate of biodegradation as described below. Suitable biodegradable polymer compositions for the shell comprise one or more of polylactic acid, polyglycolic acid, polycaprolactone, polytrimethylcarbonate, polyethylene glycol diacrylates, polyanhidrides, polyorthoesters, polyphosphazines, polyacetals, polyesters, polyureas, polycarbonates, polyurethanes, poly-alpha-hydroxy acids, polyamides, polyamino acids, and other biodegradable polymers or copolymers with an appropriate biodegradation rate and that are biocompatible.

The biodegradable polymer can be either a preformed polymer or may be polymerized at the time of deposition on the core. The biodegradable polymer layer can be tethered to the reactive layer or the core itself by methods known in the art, for example by making a slurry of the core particles in a dilute organic solution of the reactive monomers or the polymer. In one embodiment, the monomers or the polymers of the shell are chemically modified to include end groups such as peptides that are interactive with cells within the body, for example, end groups that are active in stimulating tissue repair or bone regeneration. Such end groups can include, for example, peptides containing arginine-glycine-aspartic acid sequences, signal molecules, and many of the previously described physiologically active agents such as, for example, bone morphogenic proteins.

The biodegradable shell can be selected to provide a balance between the temporal mechanical stability of the scaffold and the development of additional internal porosity. The volume ratio of the core/shell components can vary widely, from about 95/5 to 5/95, with a preferred core/shell ratio of 20/80.

After adsorption of the polymers on the core, a stabilizing agent for the suspended solids may optionally be added. The core/shell slurry may be mixed with a dilute aqueous solution containing a small amount, for example from about 0.5 wt % to about 3 wt %, of high molecular weight polyethylene glycol or polyvinyl alcohol.

When the core/shell particles are formed as a slurry, the slurry can be mixed with a calcium source, and optionally a phosphate source, to form a coating on the exterior of the polymer shell of the formed particles. Exemplary precursors for providing the calcium and optional phosphate source are a buffered water-alcohol solution of a calcium salt (e.g., calcium acetate), a calcium salt and a phosphoric acid ester, or a formulated plasma fluid. This calcium ion-doped outer coating can serve as the interface with the bioactive fibroin matrix.

The resulting core/shell particles are in a relatively stable suspension in the aqueous phase. After drying, for example, freeze-drying, the particles can be lightly milled to form a core/shell powder. Once formed, the core/shell powder can then be mixed with the fibroin solution or suspension. The water content of the mixture can be adjusted to maintain fluidity. The relative quantities of particles and fibroin solution or suspension can vary depending on the particular application. Typically, the solution or suspension can contain about 10 vol % to about 50 vol % (percent by volume), preferably about 30 vol % to about 50 vol % of the particulate phase.

Once formed, the fibroin solutions and/or suspensions can be used in vivo as a scaffold for tissue construction, or administered to an animal, for example, a mammal such as a rabbit, dog, cat, horse, human, and the like for tissue construction. As used herein, "tissue construction" is intended to include formation of hard or soft tissue that is not at the site of an injury, for example in plastic surgery, or repair or reconstruction at a site of injury.

If the fibroin suspension is in the form of an occlusion or a gel, the fibroin suspension preferably is administered to a tissue construction site by injection. A fibroin gel for injection is a reversible gel, i.e., a gel that can revert back to a less viscous state under, for example, the application of heat or mechanical stress. Mechanical stress can include the stress applied to the gel during the injection process. Alternatively, if the fibroin suspension is in the form of a cream or a paste, the fibroin suspension can be applied by placing in a tissue construction site (i.e., a site in need of tissue repair) by means such as surgical placement or by spreading (i.e., topical administration). Without being held to theory, it is believed that regardless of the mode of administration, once applied, the fibroin suspensions can form a matrix or scaffold that can permit the infiltration and growth of the cells used in tissue construction.

The fibroin solutions and suspensions can be provided to a practitioner ready for injection or other forms of administration. When mixed with particles, the characteristics of fibroin solutions and suspensions can be selected at the time of injection using a one- or two-syringe technique. In the one-syringe technique, the relative quantities of particles and fibroin solution or suspension are provided by the practitioner depending on the application, then mixed, and placed in a traditional single syringe with needle and injected. Alternatively, the particles and fibroin solution or suspension can be provided in separate cartridges and mixed in a mixing chamber prior to placement. Use of a device that allows variable mixing during placement provides the practitioner with the ability to vary the composition of the scaffold to better match the variation of properties at a given site (e.g., bone or soft tissue). The water contents of the two components are chosen to allow rapid mixing and injection.

In use, the fibroin solutions and suspensions are administered to a human or animal for a variety of purposes, for example to fill cavities, replace missing tissue, or for soft tissue or articular repair. The fibroin solution or suspension can be administered by, for example, injection or topical application (i.e., applied as a cream to the skin). Without being held to theory, in the case of a solution, it is believed that the solution can rapidly dissipate excess water into the body until quasi-equilibrium is established between the injected material and the surrounding bodily fluids, thereby producing a suspension that can form a scaffold in vivo. In the case of an occlusion, it is believed that upon placement in the body, the occlusion can undergo a transition such as a sol-gel transition, thereby producing a gel that can be in the form of a scaffold. In all cases, it is preferred that the materials, once injected, are porous.

Figure 1:
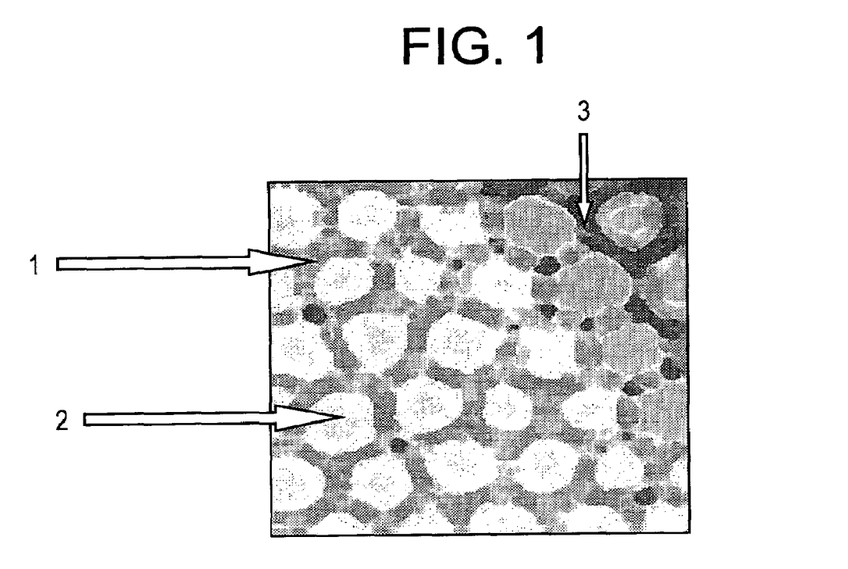
FIG. 1 is a schematic diagram of a multi-component scaffold in the process of tissue repair.

Without being held to theory, it is believed that when the injected fibroin solution or suspension comprises core/shell particles, degradation of the polymeric shells over time can generate additional porosity within the suspension, i.e., in the form of a gel, forming a scaffold that enhances infiltration and growth of the cells necessary for tissue repair. Once injected, for example, the fibroin can comprise a three-dimensional web (or honeycomb) in the form of a gel that encapsulates the dispersion of core/shell particles. FIG. 1 shows a schematic of a hypothetical three-dimensional web in the process of tissue repair. The fibroin 1 is infiltrated by cells and the core/shell particles 2 undergo at least partial degradation. The dimensions and state of aggregation of the core/shell particles control the additional porosity of the scaffold. The newly formed tissue 3 can undergo organization in the pores. The composition and morphology of the fibroin matrix are the primary factors controlling bioactivity.

A porous fibroin scaffold can promote cell adhesion, proliferation and activation, while slowly degrading during the healing process. Furthermore, degradation of the fibroin can produce peptides with molecular weights in the range of about 20 kiloDaltons or less that can be released into the surrounding biological fluid thus enhancing the metabolic activity of the surrounding cells. Without being held to theory, it is further hypothesized that thermal or proteolytic enzyme treatment can increase the biodegradation rate of fibroin by exposing specific active sites for eventual interaction with growth factors, pharmacological molecules, and peptides specific for mediation of cellular adhesion.

The above-described fibroin solutions and suspensions can be used, for example, in a variety of repair procedures for bones and tissues. Exemplary procedures include, but are not limited to, orthopedic, maxillofacial, dental, and general surgical procedures such as tumor resection and plastic surgery. For example, fibroin solutions and suspensions can be used in the repair of bone fractures via adhesive bonding, and rehabilitation of bones implicated in osteoporosis and osteoarthritis, by rehabilitating the affected bones. Such materials can also be used as bone cements (for prostheses, for example), to fill or augment tissues, to modify tissues size or shape, in periodontal pockets, as stabilizers for tooth and articular implants, and as fillings for gaps generated between hip, knee, and other prostheses and bone in order to achieve prosthesis immobilization and promote bone regeneration. Fibroin solutions and suspensions can also be used, for example, to fill pockets formed around the teeth of periodontal patients, thus permitting partial bone regrowth and possibly reducing bacterial infection; and to fill the gaps between bone and an implant such as, for example, a hip or knee implant. Filling such a gap can potentially lead to prosthesis stabilization and increase the service lifetime of the prosthesis. Fibroin solutions and suspensions can also be used to fill tissue defects such as those caused by bone tumor surgery and reconstructive surgery, and to enhance bone and tissue repair, for example to induce calcium precipitation, or osteoblast proliferation and activity, with the formation of newly formed bone tissue.

The fibroin solutions and suspensions comprising core/shell particles are especially useful for bone repair. Without being held to theory, it is believed, in this case, that the bone repair process may occur as follows. The first components to degrade may be the calcium ion-doped shells of the core/shell particles, enabling body fluids to diffuse into the calcium ion-rich water layers that serve as the interfacial zone between the biodegradable shells and the encapsulating fibroin web. The porosity of the fibroin matrix and the additional porosity created by the shell degradation enable the infiltration of osteoblast cells in the porous scaffold, which interact with the bioactive web of the scaffold and initiate new tissue and bone growth. The next stage is presumably biodegradation of the reactive layer, if present, for example by hydration of —SiO— bonds that bind the biodegradable shell to the mineral core, thus introducing the resorbable mineral core into the fluid of the remaining hydrogel. The repair process is accompanied by biodegradation of the fibroin as new bone is generated. The composite scaffold can maintain the mechanical stability of the three-dimensional, mechanically stable, high surface area web, at least during the first stages of bone regeneration.

A particularly advantageous feature of the fibroin solutions and suspensions is that the material morphology and mechanical properties are readily varied by modification of the bioactive matrix and the core/shell biodegradable particles to meet the requirements of specific applications. It is contemplated that bioactive, biodegradable gels and polymers other than fibroin can be used in combination with the core/shell particles described herein to form scaffolds.

Fibroin solutions, suspensions, and composites can induce proliferation in such cell types as osteoblasts, keratinocytes, fibroblasts, pericytes, endothelial cells, and the like. Because fibroin solutions and suspensions can enhance the proliferation of many cell types, they can also be used in applications involving tissues other than bone tissue, for example, for soft tissue reconstruction such as after plastic surgery, artificial skin applications, cartilage repair, and the like.

The invention is further illustrated by the following non-limiting Examples.

EXAMPLES

Example 1

Purification of Silk Fibroin

Using techniques known in the art, cocoons of the *Bombyx-mori* silk worm were first degummed. The glue-like sericin proteins were extracted by repeated washing in aqueous solutions of sodium carbonate ($Na_2CO_3$), as follows. The cocoons were first washed in an aqueous solution of 1.1 g/l (grams per liter) $Na_2CO_3$ at 98° C. for one hour, and then rinsed in an aqueous solution containing 0.4 g/l $Na_2CO_3$ at 98° C. for one hour. The cocoons were then washed repeatedly in distilled water at temperatures decreasing from 98° C. to ambient, leaving behind sericin-free fibroin. The amount of raw fibroin in the water was 10 g/l. The degummed fibroin was then dissolved at 65° C. in a 9.3 molar aqueous solution of lithium bromide (LiBr) for 3 hours at an initial composition of 100 g fibroin/l solution. When dissolution was complete, the aqueous solution was diluted to 5% weight/volume fibroin by the addition of distilled water. The remaining impurities and undissolved fiber were removed by filtration, using a filter with pore size n.1. The salt was then removed from the fibroin mixture by 72 hours of dialysis against distilled water, using a regenerated cellulose membrane with a molecular weight cut-off of 3,500. The final concentration of dialyzed fibroin was 1-2% pure silk fibroin.

Example 2

Formation of a Suspension by Thermal Treatment of an Aqueous Solution of Fibroin An aqueous fibroin solution (20 ml (milliliters)) was poured into a polystyrene capsule incubated at temperatures of −20° C. to 50° C. for periods of 2 to 24 hours. The solutions incubated at −20° C. were heated to and maintained at room temperature until gelation occurred. Other fibroin solutions kept at constant temperatures from 4° C. to 50° C., required incubation periods of 2 to 24 hours for gelation to occur. The water content of the gels, as determined by thermogravimetric analysis, varied from 95 to 98 wt %. The consistency of the suspensions was dependent upon the time and temperature at which they were incubated. Thus, it was demonstrated that the rheological properties of the fibroin could be varied by thermal treatment.

Example 3

Enzymatic Treatment of the Silk Fibroin

The aqueous fibroin mixture was treated with various proteolytic enzymes that are specific for reaction with bond sites of particular amino acids. The goal was to reduce the average molecular weight, to increase the biodegradation rate, and to expose specific active sites for eventual interaction with peptides specific for mediation with cellular adhesion factors, growth factors and pharmacological molecules. The following enzymes were studied:

Protease (from *Steptomyces griseus*): This enzyme hydrolyzes the peptide bonds at carboxylic sites of glutamic acid. It has been demonstrated that peptide chains of fibroin having terminal end groups of glutamic acid impede the formation of the ordered beta structure of the silk fibroin. The enzymatic reactions were performed at enzymesubstrate concentrations of 50 µl/ml (microliters/milliliter) and after one hour at 37° C. the solution becomes white in color and more viscous. The sol that is formed is an injectable material capable of forming a gel. Heating to 50° C. for 15 minutes deactivated the enzyme. The glutamic amino acid content within the fibroin protein chain was found to be approximately 1%, as determined by electrophoretic analysis. There was a notable presence of peptides with lower molecular weight than was present in the fibroin mixture prior to treatment.

Papain: This enzyme is specific for reaction with chemical bonds of leucine (0.5% of the fibroin) and glycine (44% of the fibroin). The conditions of treatment and the enzyme-substrate concentration ratio can be varied to produce different levels of viscosity of the resulting fibroin sol or solution. In this case, the product contains peptides with molecular weights in the range of 20 kD to 2 kD, as determined by electrophoretic analysis.

Chymotripsin: Treatment with this enzyme causes hydrolysis of the disulfide bond that connects the Cp (heavy) fraction (composed principally of Glycine-Alanine-Serine) and the Cs fraction (light; a mixture of short peptide chains) comprising the other amino acids present in the pure fibroin material. A buffered enzyme solution was added to the fibroin-water solution at 40° C. The degree of hydrolysis was controlled by the time of reaction. Different treatment times could trigger different amounts of hydrolysis. At completion of the reaction, the resulting aqueous medium contained the Cs or light fraction in solution and a gelatinous precipitate of the Cp or heavy fraction.

Example 4

Formation of a Suspension by the Addition of Acids or Alcohols to the Fibroin Solution Gelation was induced by adding citric acid or glycerol to the fibroin solution.

Figure 2:
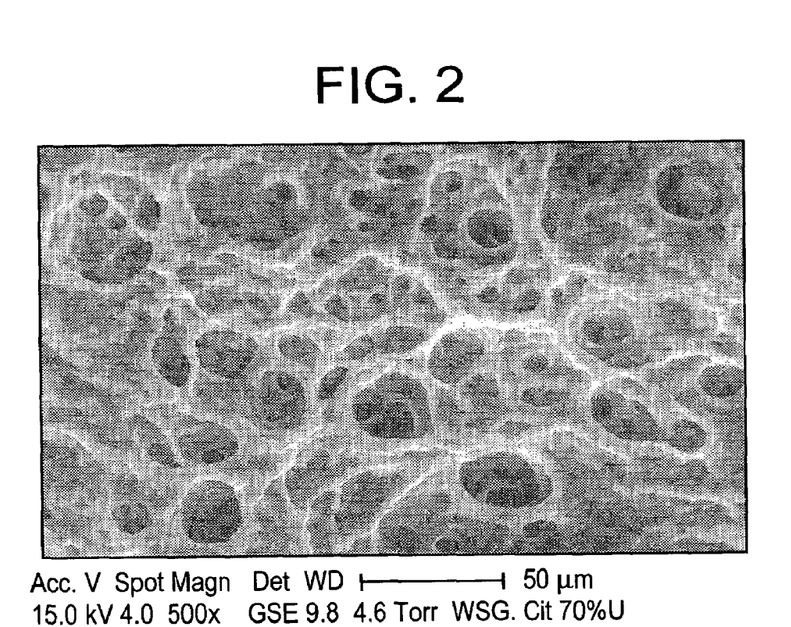
FIG. 2 is an environmental scanning electron micrograph of a fibroin suspension made by adding a water solution of citric acid to a fibroin-water solution.

Citric acid was added drop by drop to 10 ml of fibroin solutions, until the pH reached 3.7 (the isoelectric point equals 3.8). Gelation occurred after about 6 hours, producing a white, opaque porous gel that contained about 95 wt % of water. FIG. 2 shows an environmental scanning electron micrograph of the material formed.

Figure 3:
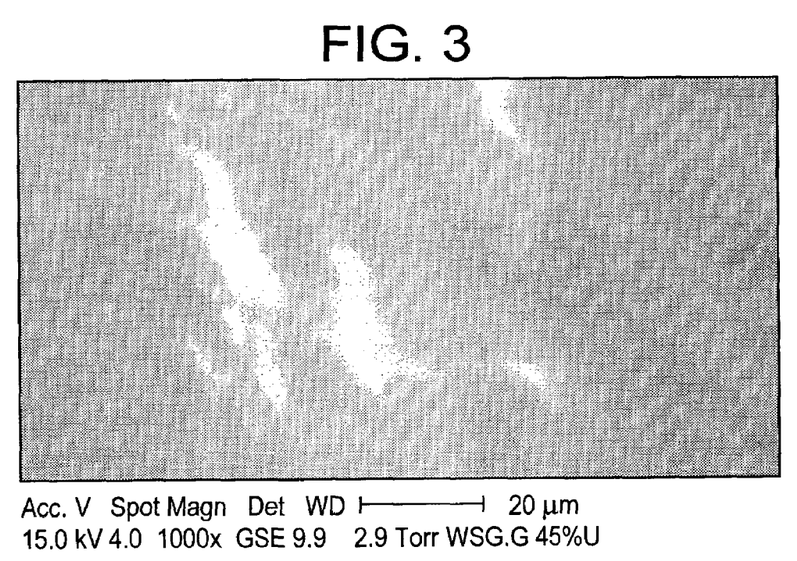
FIG. 3 is an environmental scanning electron micrograph of a fibroin suspension made by adding glycerol to fibroin-water solution.
Figure 4:
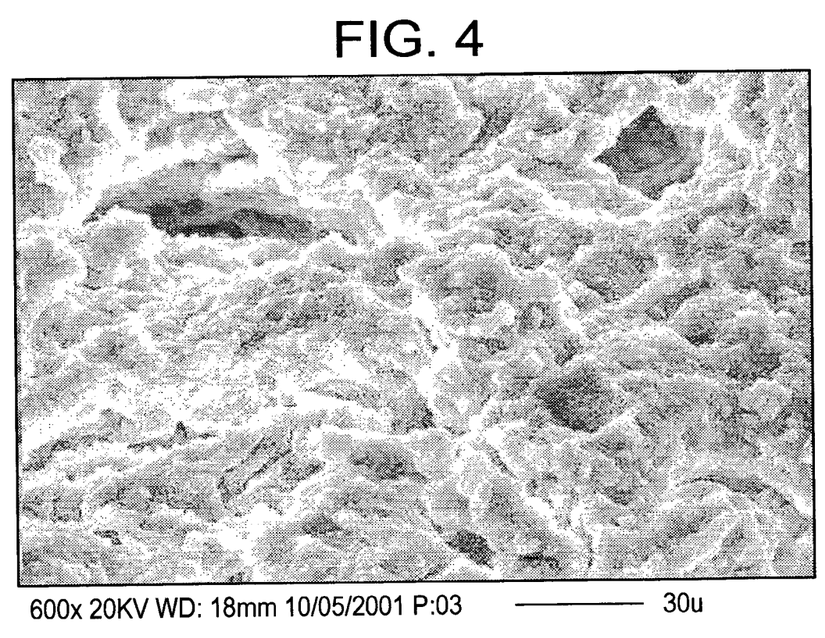
FIG. 4 is an optical micrograph of a fibroin composite suspension comprising hydroxyapatite/(poly)lactide core/shell particles embedded in a fibroin matrix after the composite was dried at room temperature.
Figure 5:
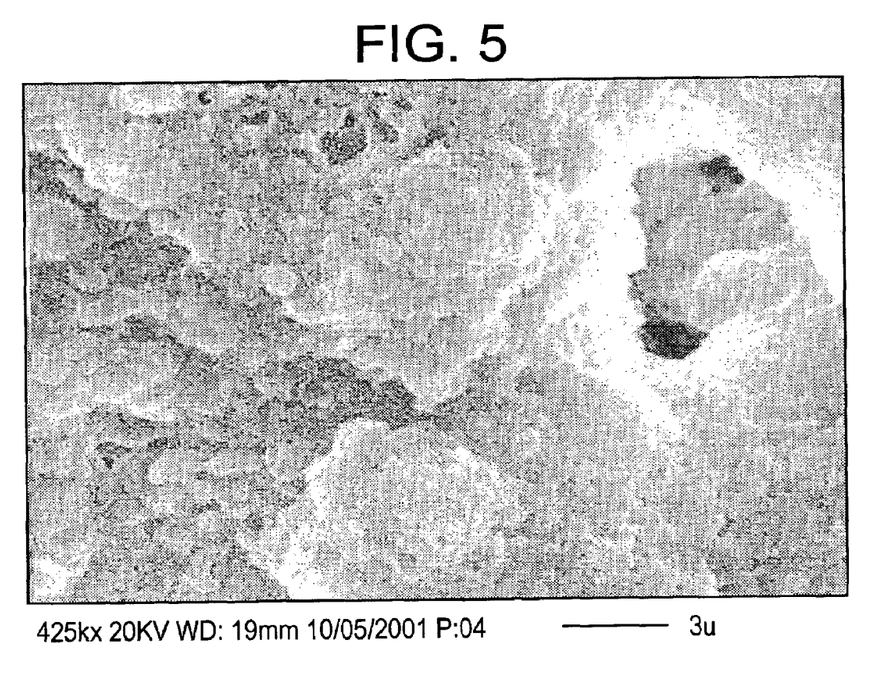
FIG. 5 is an optical micrograph of a fibroin composite suspension comprising hydroxyapatite/(poly)lactide core/shell particles embedded in a fibroin matrix after the composite was dried at room temperature, at higher magnification.
Figure 6:
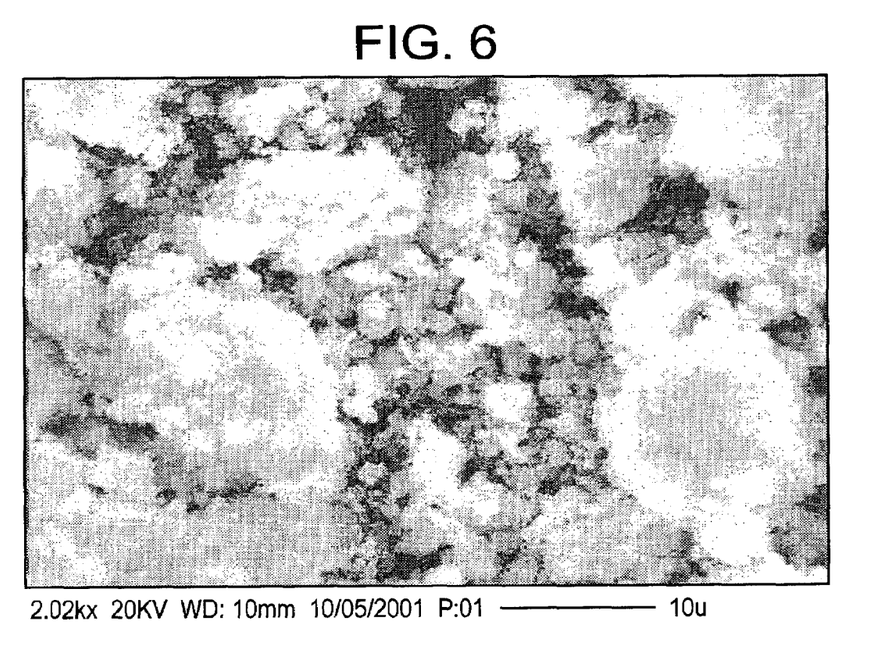
FIG. 6 is an optical micrograph of a fibroin composite suspension comprising hydroxyapatite/(poly)lactide core/shell particles embedded in a fibroin matrix after the composite was freeze-dried.
Figure 7:
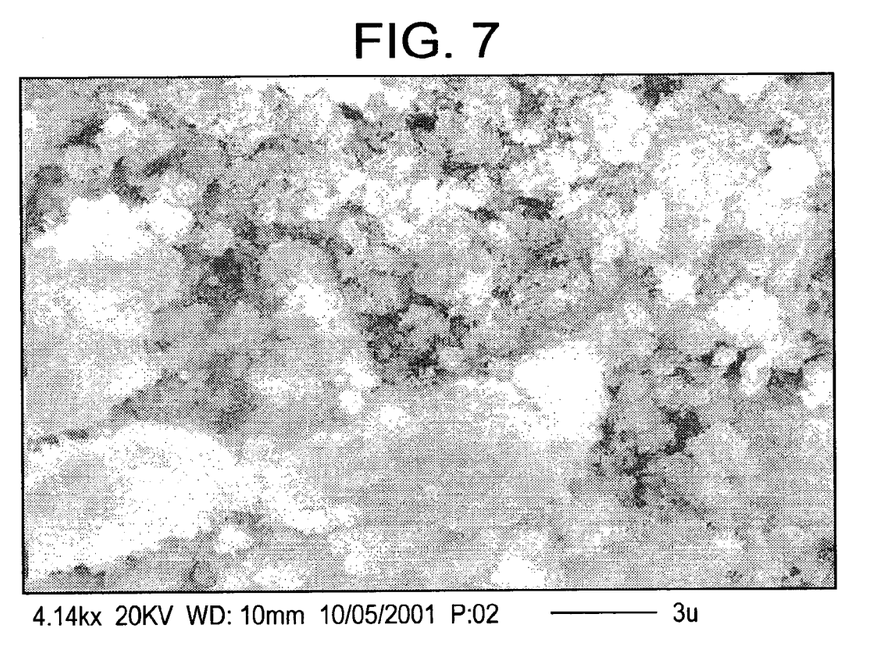
FIG. 7 is an optical micrograph of a fibroin composite suspension comprising hydroxyapatite/(poly)lactide core/shell particles embedded in a fibroin matrix after the composite was freeze-dried, at higher magnification.

When 3 ml of glycerol were added to 7 ml of fibroin solution, gelation occurred in about 20 hours, producing a white translucent gel containing about 90 wt % of water. FIG. 3 shows an environmental scanning electron micrograph of the material formed.

Example 5

In Vitro Preparation of an Injectable Fibroin Gel/Hydroxyapatite/Poly(lactide) Composite Scaffold A powder of core/shell particles of polymer-coated hydroxyapatite particles was made. A (poly)lactide (PLA) with a molecular weight of approximately 6,000 was used as the shell of biodegradable polymer. Two grams of silane-treated hydroxyapatite was added to 6 grams of a polylactide in 50 ml of butanol. The solution was heated to 70° C. for 2 hours, cooled to room temperature and mixed with 50 ml of a 2% weight/volume aqueous solution of polyethylene glycol. The settling rate of the coated particles was slow enough to maintain relative uniformity of the coating process. The core/shell mixture was stirred, poured into a glass Petrie dish, dried at 50° C. and lightly milled to a powder. The resulting material was a rather broad size distribution of spherical, polymer-coated aggregates.

Two grams of the core/shell powder were mixed with 10 ml of fibroin gel. The powder dispersed readily in the gel to form paste. The paste containing core/shell particles was dried in two ways, namely freeze-dried and also slowly dried at room temperature. FIGS. 4 to 7 are optical micrographs of the resulting scaffolds. Upon slow drying at room temperature, a particle-filled fibroin material with apparent structural integrity is formed. The freeze-dried sample exhibits the morphological structure that one might expect, namely a broad distribution of fibroin-coated.

Example 6

In Vitro Tests of Fibroin Suspensions

Human osteoblast-like cells (MG63) were cultivated for 72 hours on fibroin gels made by adding glycerol to an aqueous fibroin solution and by treating the aqueous fibroin solution at 4° C. Biochemical and immunoenzymatic parameters of MG63, grown on the tested materials and on an empty polystyrene well used as a control, were evaluated to determine cell proliferation and activity.

Cell proliferation on the pure fibroin gel prepared by thermal treatment was significantly lower when compared to the control, but, at the same time, the gel favored osteoblast activity and differentiation, as demonstrated by the enhanced ALP (alkaline phosphatase) activity (16.71+/−1.80 vs. control 10.10+/−1.61) and TGFβ1 (transforming growth factor β1) levels, (487+/−29 vs. control 432+/−42), respectively. Cell proliferation on the gel prepared by adding glycerol showed little difference when compared to the control.

Neither gel induced cytotoxicity, as revealed by the LDH (lactate dehydrogenase) level (pure fibroin gel, 14.67+/−2.04; gel with glycerol, 18.03+/−0.23; control, 14.63+/−2.19).

Example 7

In Vivo Tests of Fibroin Suspensions

Citric acid derived fibroin gels were implanted in cavities (6 mm diameter, 10 mm depth) drilled in the femoral condyle of rabbits. Implant-free cavities were used as a control. Rabbits were sacrificed after a month from implantation, and histological results of the implant sites were compared to those of the implant-free sites.

Figure 8A:
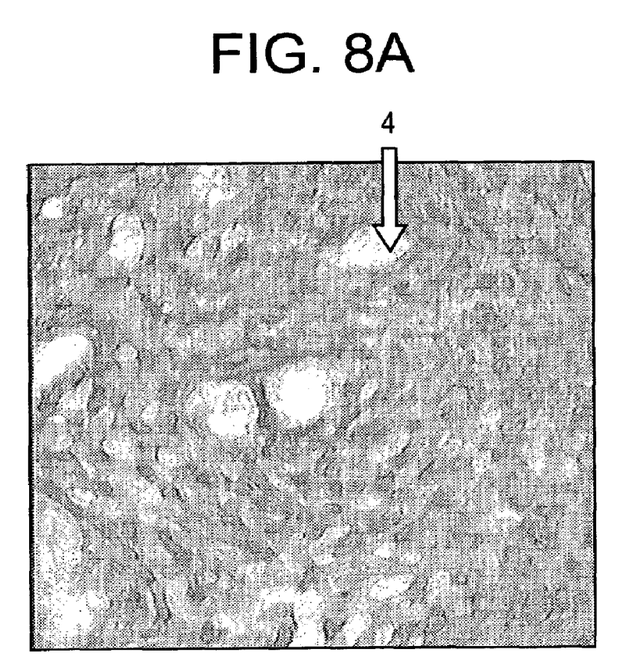
FIG. 8 compares the histologies after one month of implantation in a cavity drilled in the femur of a rabbit and filled by an injectable fibroin suspension (A) to that of an empty cavity used as a control (B).
Figure 8B:
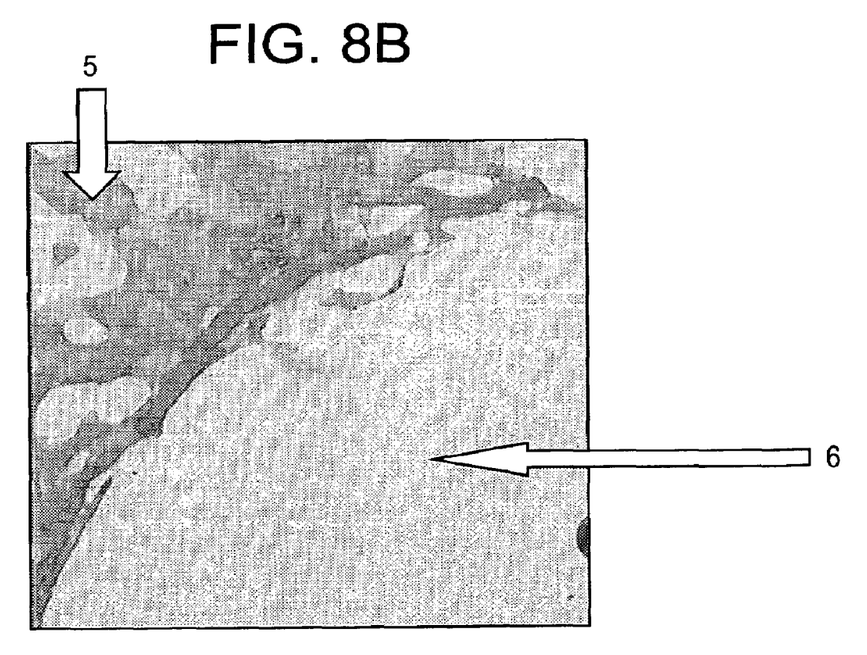
Figure 9A:
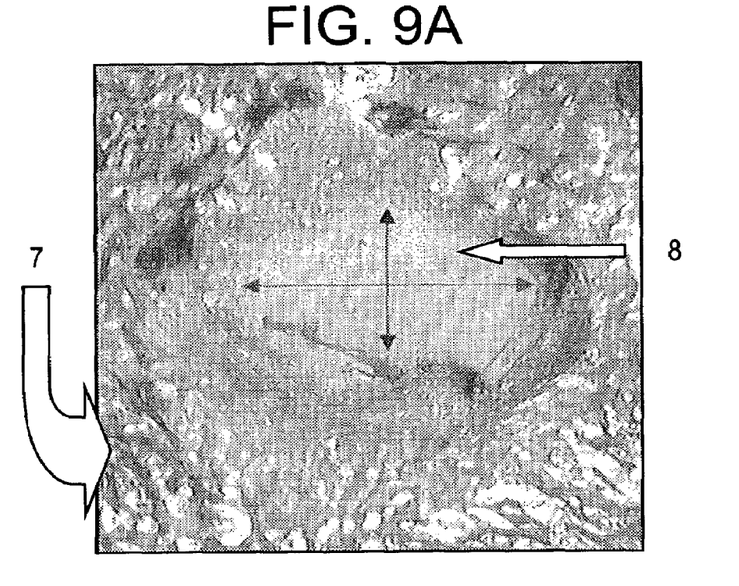
FIG. 9 compares the histologies after one month of implantation in a cavity drilled in the femur of a second rabbit filled by an injectable fibroin suspension (A) to that of an empty cavity used as a control (B).
Figure 9B:
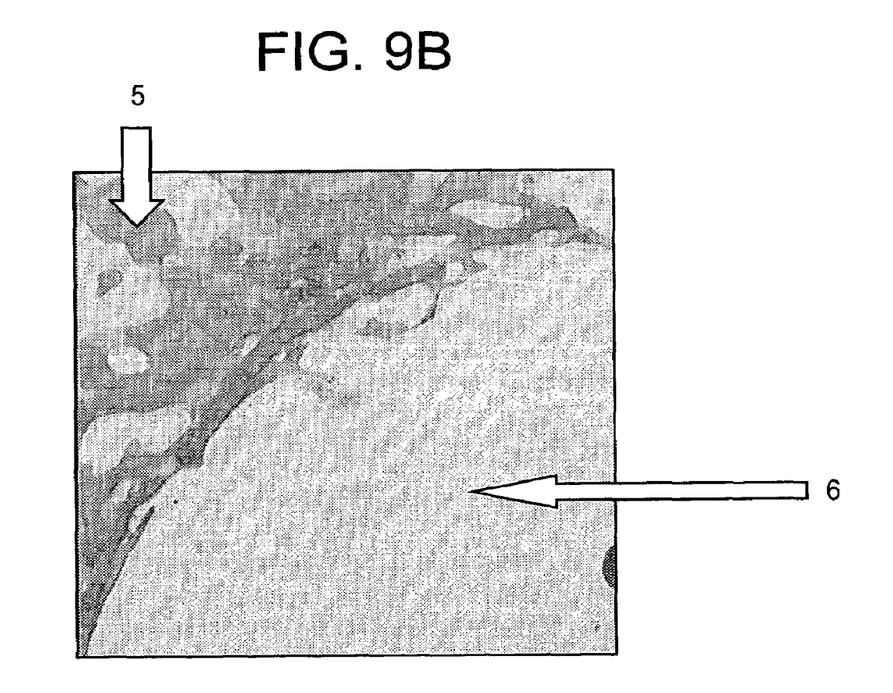
Figure 10:
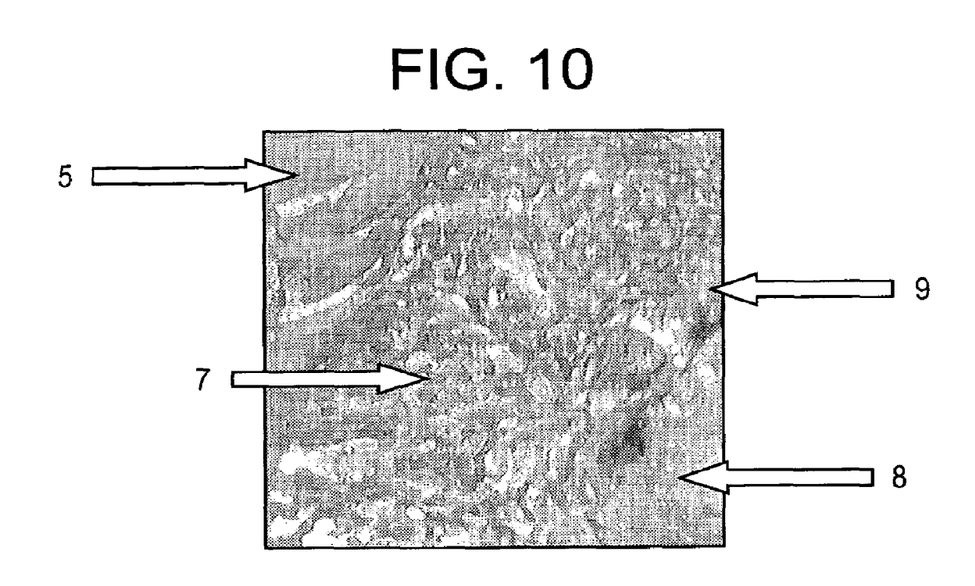
FIG. 10 shows the interface between the old bone and the new bone formed in the fibroin suspension filled cavity of the implant illustrated in FIG. 9.

After one month of implantation, the hole in one cavity filled by the fibroin gel was completely filled by newly formed bone (FIG. 8A). Nearly complete bone healing with some residual fibroin 4 was observed. The cavity with no fibroin added displayed no bone regeneration (see FIG. 8B). The original bone 5 and the empty defect 6 were observed. In four of the cavities filled with the fibroin gel, the cavities were nearly filled with newly formed bone 7, with small residual cavities 8 being still present (FIG. 9A). In FIG. 9A, the cavity has a width of 1.08 millimeters and a length of 1.7 millimeters. FIG. 10 shows the interface between the original bone 5 and the newly grown bone 7. The new bone formed well-organized trabeculae that propagated from the original bone trabeculae without creating any gap between the newly-formed and the original bone. A residual cavity 8 was observed as was connective tissue undergoing mineralization 9. A mild inflammation was observed, with the absence of any granuloma and apparent adverse immunological response. Only fragments of the original fibroin gel were still visible, confirming the ability of the gel to degrade at a rate that is compatible with the rate of tissue regeneration, thus providing evidence that the fibroin suspensions are useful for the proposed applications.

Novel fibroin suspensions and composites, have been disclosed. Such fibroin suspensions can be made from a solution of purified fibroin using heat, proteolytic enzymes, acids, alcohols, or a biocompatible polymer. The fibroin suspensions can be in the form of occlusions, gels, creams or pastes. The fibroin suspensions and composites as well as solutions have particular utility as for use in bone and tissue construction, repair and regeneration. Because the fibroin solutions, suspensions, and composites can be injected, the need for many invasive surgical procedures, particularly orthopedic procedures can be reduced, thus minimizing the potential for infection decreasing the required recovery periods and lowering the overall cost of the medical procedures.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A composition comprising a fibroin suspension wherein the fibroin suspension is injectable and bioactive, wherein the fibroin suspension further comprises a pore-forming particle comprising a core-shell particle, and wherein the cores have dimensions from about 1 nanometer to about 500 micrometers in their largest diameter.

2. The composition of claim 1, wherein the fibroin comprises a *Bombyx mori* silkworm fibroin.

3. The composition of claim 1, wherein the fibroin comprises a proteolytically degraded fibroin.

4. The composition of claim 1, wherein the core comprises a hydroxyapatite, a calcium phosphate-based mineral, a resorbable glass filler, or a combination comprising one or more of the foregoing materials.

5. The composition of claim 4, wherein the core additionally comprises a reactive layer.

6. The composition of claim 1, wherein the shell comprises a biodegradable polymer.

7. The composition of claim 6, wherein the biodegradable polymer comprises polylactic acid, polyglycolic acid, polycaprolactone, polytrimethylcarbonate, polyethylene glycol diacrylates, polyanhidrides, polyorthoesters, polyphosphazines, polyacetals, polyesters, polyureas, polycarbonates, polyurethanes, polyalpha-hydroxy acids, polyamides, polyamino acids, or a combination of one or more of the foregoing biodegradable polymers.

8. The composition of claim 7, wherein the biodegradable polymer is modified with one or more end groups reactive with the cells of the body to stimulate tissue repair.

9. The composition of claim 1, wherein the core/shell particle further comprises a calcium source, wherein said calcium source is coated on the exterior of the polymer shell of the formed particles.

10. The composition of claim 9, wherein the core/shell particle further comprises a phosphate source, wherein said phosphate source is coated on the exterior of the polymer shell of the formed particles.

11. The composition of claim 1, wherein the fibroin suspension further comprises a physiologically active agent.

12. The composition of claim 11, wherein the physiologically active agent comprises antibiotics, bone morphogenic proteins, growth factors, compounds that stimulate wound repair, or a combination of one or more of the foregoing agents.

13. A method for the formation of a fibroin suspension, comprising:
heating a fibroin solution from about −20° C. to about 50° C. to form a fibroin suspension, wherein the fibroin suspension is injectable and bioactive; and
adding a core-shell particle, a physiologically active agent, or a combination comprising one or more of the foregoing to the fibroin suspension,
wherein the cores have dimensions from about 1 nanometer to about 500 micrometers in their largest diameter.

14. A method for the formation of a fibroin suspension, comprising:
treating a fibroin solution with an agent comprising an acid, an alcohol, a proteolytic enzyme, a biocompatible polymer, or a combination comprising one or more of the foregoing agents, to form a fibroin suspension, and
mixing core-shell particles into the fibroin suspension, wherein the cores have dimensions from about 1 nanometer to about 500 micrometers in their largest diameter.

15. The method of claim 14, wherein the alcohol comprises glycerol.

16. The method of claim 14, wherein the acid comprises citric acid, ascorbic acid, lactic acid, or a combination of one or more of the foregoing acids.

17. The method of claim 14, wherein the biocompatible polymer comprises polyethyleneglycol, polyethyleneoxide, polyvinylpyrrolidone, or a combination of one or more of the foregoing biocompatible polymers.

18. The method of claim 14, wherein the proteolytic enzyme comprises the protease from *Streptomyces griseus*, papain, chymotrypsin, or a combination of one or more of the foregoing proteolytic enzymes.

19. The method of claim 14, further comprising adding a physiologically active agent to the fibroin material.

20. A method of tissue construction, comprising administering to a site to be constructed a fibroin solution or suspension in an amount effective to stimulate tissue formation;
wherein the fibroin solution or suspension is injectable and bioactive,
wherein the fibroin solution or suspension further comprises a pore-forming particle comprising a core-shell particle, and
wherein the cores have dimensions from about 1 nanometer to about 500 micrometers in their largest diameter.

21. The method of claim 20, wherein the fibroin suspension further comprises at least one physiologically active agent.

22. The method of claim 21, wherein the physiologically active agent comprises antibiotics, bone morphogenic proteins, growth factors, compounds that stimulate wound repair, or a combination of one or more of the foregoing agents.

23. The method of claim 20, wherein the site comprises a periodontal cavity, a product of a tumor resection, a product of a plastic surgery, or a cavity between a bone and a prosthesis.

24. The method of claim 20, wherein the tissue is bone.

25. The method of claim 24, wherein the construction is bone repair, comprising cementing bone for a prosthesis, bone repair associated with osteoporosis, bone repair associated with osteoarthritis, bone repair of fractures, stabilization of a tooth implant, or a combination of one or more of the foregoing repairs.

26. The method of claim 20, wherein administering is injecting.

27. The method of claim 20, wherein administering is performed topically.

28. A method to induce cell proliferation, comprising contacting a cell with a fibroin solution or suspension in an amount effective to induce cell proliferation;
wherein the fibroin solution or suspension is injectable and bioactive,
wherein the fibroin solution or suspension further comprises a pore-forming particle comprising a core-shell particle, and
wherein the cores have dimensions from about 1 nanometer to about 500 micrometers in their largest diameter.

29. The method of claim 28, wherein the fibroin suspension further comprises at least one physiologically active agent.

30. The method of claim 28, wherein the cell comprises an osteoblast, a keratinocyte, a fibroblast, a pericyte, a chondrocyte, or an endothelial cell.

* * * * *